(12) United States Patent
Aoki et al.

(10) Patent No.: US 7,745,977 B2
(45) Date of Patent: Jun. 29, 2010

(54) ULTRASONIC PROBE

(75) Inventors: Minoru Aoki, Nasushiobara (JP);
Hiroyuki Shikata, Nasushiobara (JP);
Takashi Takeuchi, Otawara (JP);
Yasuhisa Makita, Nasushiobara (JP);
Koichi Shibamoto, Otawara (JP)

(73) Assignees: Kabushiki Kaisha Toshiba, Tokyo (JP);
Toshiba Medical Systems Corporation, Otawara-shi (JP)

(*) Notice: Subject to any disclaimer, the term of this patent is extended or adjusted under 35 U.S.C. 154(b) by 587 days.

(21) Appl. No.: 11/614,581

(22) Filed: Dec. 21, 2006

(65) Prior Publication Data
US 2007/0145860 A1 Jun. 28, 2007

(30) Foreign Application Priority Data
Dec. 22, 2005 (JP) .............................. 2005-370817

(51) Int. Cl.
*H01L 41/04* (2006.01)
*H01L 41/08* (2006.01)
(52) U.S. Cl. ...................................... 310/334; 310/365
(58) Field of Classification Search ................. 310/365, 310/334
See application file for complete search history.

(56) References Cited
U.S. PATENT DOCUMENTS
4,217,684 A 8/1980 Brisken et al.

2001/0041837 A1* 11/2001 Takeuchi et al. ............ 600/437
2005/0070801 A1* 3/2005 Yamashita et al. .......... 600/459
2008/0312537 A1* 12/2008 Hyuga ........................ 600/459
2009/0069689 A1* 3/2009 Isono .......................... 600/459

FOREIGN PATENT DOCUMENTS
JP 11-151239 6/1999

* cited by examiner

*Primary Examiner*—J. SanMartin
(74) *Attorney, Agent, or Firm*—Oblon, Spivak, McClelland, Maier & Neustadt, L.L.P.

(57) ABSTRACT

An ultrasonic probe is provided which includes a piezoelectric vibrator having an earth electrode and a signal electrode on a rear surface, an acoustic matching layer disposed on a front surface side of the piezoelectric vibrator, a packing material disposed on the rear surface of the piezoelectric vibrator, and a flexible printed circuit that is interposed between the piezoelectric vibrator and the packing material to cover the entire rear surface of the piezoelectric vibrator and has an earth wiring layer and a signal wiring layer. The earth wiring layer and the signal wiring layer are exposed from a surface facing the piezoelectric vibrator of the flexible printed circuit so as to be electrically connected to the earth electrode and the signal electrode through an exposed surface of the earth wiring layer and an exposed surface of the signal wiring layer, respectively.

7 Claims, 3 Drawing Sheets

ULTRASONIC PROBE

CROSS-REFERENCE TO RELATED APPLICATIONS

This application is based upon and claims the benefit of priority from prior Japanese Patent Application No. 2005-370817, filed Dec. 22, 2005, the entire contents of which are incorporated herein by reference.

BACKGROUND OF THE INVENTION

1. Field of the Invention

The present invention relates to an ultrasonic probe that is connected to an ultrasonic diagnostic instrument so as to transmit and receive ultrasonic waves to and from a sample.

2. Description of the Related Art

An ultrasonic probe is a device that is used for imaging the internal state of a sample by irradiating ultrasonic waves toward the sample and receiving a wave reflected from an interface having different acoustic impedance in the sample. Such ultrasonic probe is employed to, for example, an ultrasonic diagnostic instrument that inspects the interior of a human body.

The ultrasonic probe in the related art is configured of a piezoelectric vibrator, an acoustic matching layer disposed at a front surface of the piezoelectric vibrator, a backing material disposed at a rear surface of the piezoelectric vibrator, and a flexible printed circuit (FPC) connected to the piezoelectric vibrator. The piezoelectric vibrator includes earth electrode and signal electrode each connected to the front surface and the rear surface thereof. The piezoelectric vibrator generates the ultrasonic waves for scanning the sample on the basis of the voltage applied from the earth electrode and the signal electrode.

By this way, two methods are mainly used for the connection between the piezoelectric vibrator and the flexible printed circuit.

As a first technique, by drawing out the earth electrode into the rear surface of the piezoelectric vibrator, earth wiring of the piezoelectric vibrator is connected to the flexible printed circuit at the rear surface of the piezoelectric vibrator through a portion of the earth electrode drawn out into the rear surface of the piezoelectric vibrator (see, for example, JP-A-11-151239).

As a second technique, by forming a plating electrode on the entire surface of the acoustic matching layer, the earth wiring of the piezoelectric vibrator is connected to the flexible printed circuit at the front surface of the piezoelectric vibrator through the plating electrode. The acoustic matching layer having conductive property may be used. In this case, the plating electrode is unnecessary.

In addition, in both of the first and second techniques, the signal electrode of the piezoelectric vibrator and the flexible printed circuit is connected to each other at the rear surface of the piezoelectric vibrator.

By the way, in the first technique, the wiring between the earth electrode of the piezoelectric vibrator and the flexible printed circuit is electrically connected by a soldering process. For this reason, a piezoelectric material used in the piezoelectric vibrator is likely to be deteriorated by the influence of heat.

In addition, in the first technique, a notched portion is formed at the side of the packing material. The flexible printed circuit is inserted into the notched portion. For this reason, the piezoelectric vibrator is floating in the notched portion. As a result, during the joint of the piezoelectric vibrator and the packing material, if the piezoelectric vibrator is pressurized against the packing material, biased pressurization is applied to the piezoelectric vibrator. Therefore, the piezoelectric vibrator may be cracked.

Furthermore, in the first technique, the earth electrode of the piezoelectric vibrator and the flexible printed circuit are connected to each other at one location. For this reason, the electric joint reliability between the earth electrode of the piezoelectric vibrator and the flexible printed circuit is low.

Further, in the second technique, the metal having high acoustic impedance is used as the plating electrode formed on the surface of the acoustic matching layer. For this reason, the conditions of the acoustic matching fall into disorder by the plating electrode existing in a propagation path of the ultrasonic waves. Therefore, acoustic characteristics may be decreased.

Furthermore, in the second technique, since the acoustic matching layer having the conductive property DOES not necessarily have the acoustic impedance of the desire, sufficient acoustic matching conditions may not be obtained by the restriction of materials.

BRIEF SUMMARY OF THE INVENTION

The present invention has been made in view of the above circumstance and is aimed at providing an ultrasonic probe having high reliability and good acoustic property while a piezoelectric vibrator is not easily damaged.

According to an aspect of the invention, there is provided an ultrasonic probe including a piezoelectric vibrator having a first electrode and a second electrode on a rear surface; an acoustic matching layer disposed on a front surface of the piezoelectric vibrator; a packing material disposed on the rear surface side of the piezoelectric vibrator; and a flexible printed circuit that is interposed between the piezoelectric vibrator and the packing material to cover the entire rear surface of the piezoelectric vibrator and has a first wiring layer and a second wiring layer. In this configuration, the first wiring layer and the second wiring layer may be exposed from a surface facing the piezoelectric vibrator of the flexible printed circuit so as to be electrically connected to the first electrode and the second electrode through an exposed surface of the first wiring layer and an exposed surface of the second wiring layer, respectively.

According to another aspect of the invention, there is provided an ultrasonic probe including: a piezoelectric vibrator transmitting and receiving ultrasonic waves; an acoustic matching layer disposed on a front surface of the piezoelectric vibrator; a packing material disposed on a rear surface of the piezoelectric vibrator; and a flexible printed circuit that is interposed between the piezoelectric vibrator and the packing material to cover the entire rear surface of the piezoelectric vibrator and has a first wiring layer and a second wiring layer. Here, the piezoelectric vibrator includes: a piezoelectric body having an piezoelectric effect; a first electrode formed at a part on a rear surface of the piezoelectric body; and a second electrode having a first portion formed on a front surface of the piezoelectric body and a second portion formed on the rear surface of the piezoelectric body and positioned on both sides of the first electrode. In this configuration, the first wiring layer is exposed from the flexible printed circuit at a part facing the first electrode, and the second wiring layer is exposed from the flexible printed circuit at a part facing the second portion of the second electrode. The first wiring layer and the second wiring layer are electrically connected to the first electrode and the second electrode through an exposed surface of the first wiring layer and an exposed surface of the second wiring layer, respectively.

According to another aspect of the invention, there is provided an ultrasonic probe including a plurality of piezoelectric bodies; a first electrode formed at a first surface of each piezoelectric body; a second electrode having a first portion formed at the first surface of each piezoelectric body such that the first electrode is disposed therebetween, a second portion formed at a second surface facing the first surface of each piezoelectric body, and a third portion electrically connecting between the first portion and the second portion; an acoustic matching layer disposed at a side of the second surface of each piezoelectric body; and a flexible printed circuit provided at a side of the first surface of each piezoelectric body and has a first wiring layer connected to each of the first electrode and a second wiring layer connected to each of the second electrode.

DETAILED DESCRIPTION OF THE INVENTION

Hereinafter, embodiments of the invention will be described with reference to FIGS. 1 to 5.

Configuration of Ultrasonic Probe

Figure 1:
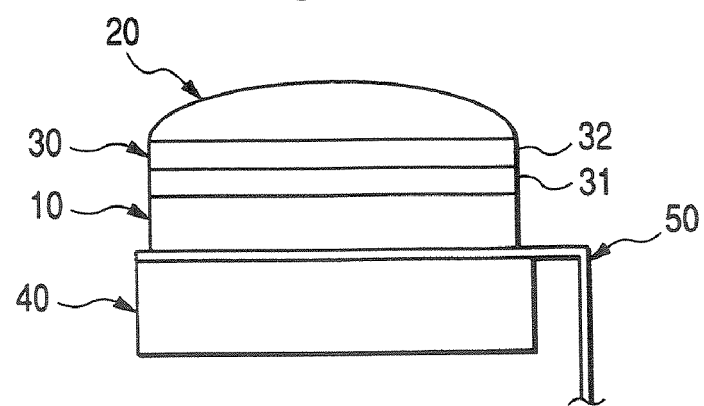
FIG. 1 is a schematic view of an ultrasonic probe according to an embodiment of the present invent.

FIG. 1 is a schematic view of an ultrasonic probe according to an embodiment of the present invention.

As shown in FIG. 1, the ultrasonic probe according to the embodiment of the invention transmits and receives ultrasonic waves in the direction of an axis center of the probe. The ultrasonic probe mainly includes a piezoelectric vibrator 10, an acoustic lens 20, an acoustic matching layer 30, a packing material 40, and a flexible printed circuit 50. Furthermore, in the following description, the direction where the ultrasonic waves are scanned is referred to as a scan direction (the direction perpendicular to a space), and the direction where the ultrasonic waves are focused is referred to as a lens direction (the right and left directions of the space)

Piezoelectric Vibrator

Figure 2:
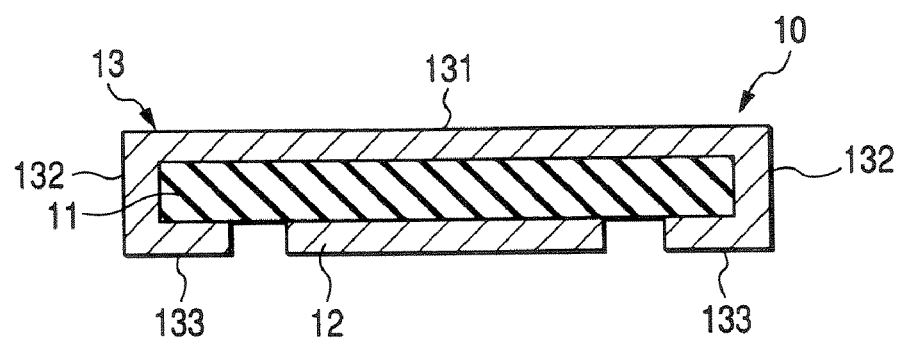
FIG. 2 is a cross-sectional view of a piezoelectric vibrator according to the embodiment of the invention.

FIG. 2 is a cross-sectional view of a piezoelectric vibrator 10 according to the embodiment of the invention.

As shown in FIG. 2, the piezoelectric vibrator 10 includes a piezoelectric body 11 having piezoelectric effects, a signal electrode (a second electrode) 12 for applying a signal voltage to the piezoelectric body 11, and an earth electrode (a first electrode) 13 for applying an earth voltage to the piezoelectric body 11.

The piezoelectric body 11 is divided into a plurality of elements in the scan direction. The thickness of the piezoelectric body 11 is about 100 μm to 500 μm. As a material of the piezoelectric body 11, a piezoelectric ceramics, for example, such as PZT is used.

The signal electrode 12 is formed at the rear surface of the piezoelectric body 11. The forming range of the signal electrode 12 is confined to the inner side rather than the outer edge of the rear surface of the piezoelectric body 11 in the lens direction. That is, the area where the signal electrode 12 is not formed exists in the vicinity of the outer edge relative to the lens direction of the rear surface of the piezoelectric body 11. As a material of the signal electrode 12, metals such as gold and silver having a good conductive property are used.

The earth electrode 13 is provided with a front electrode portion (a first portion) 131 formed at the front surface of the piezoelectric body 11, side electrode portions 132 formed at both sides of the lens direction of the piezoelectric body 11, and rear electrode portions (a second portion) 133 formed at the rear surface of the piezoelectric body 11. The front electrode portion 131, the side electrode portions 132, and the rear electrode portions 133 are electrically connected to each other. As a material of the earth electrode 13, metals such as gold and silver having a good conductive property are used.

The rear electrode portions 133 are each formed at both sides of the lens direction such that the signal electrode 12 is interposed therebetween. That is, the rear electrode portion 133 is formed in the area where the signal electrode 12 is not formed in the rear surface of the piezoelectric body 11.

Acoustic Lens

The acoustic lens 20 (see FIG. 1) serves to focus the ultrasonic waves that are transmitted and received and forms the focused ultrasonic waves into a beam shape. The acoustic lens 20 is disposed at the front surface of the acoustic matching layer 30. As a material of the acoustic lens 20, for example, silicone having the acoustic impedance that is near a living body is used.

Acoustic Matching Layer

The acoustic matching layer 30 (see FIG. 1) serves to acoustically match the piezoelectric vibrator 10 and the acoustic lens 20 and is disposed between the piezoelectric vibrator 10 and the acoustic lens 20. The acoustic matching layer 30 includes a first matching layer 31 and a second matching layer 32. A material of the first matching layer 31 and the second matching layer 32 is not especially limited. However, the material of the first matching layer 31 and the second matching layer 32 may be selected such that the acoustic impedance is changed gradually from the piezoelectric vibrator 10 toward the acoustic lens 20.

Packing Material

The packing material 40 serves to absorb the ultrasonic waves for propagating into the rear surface of the piezoelectric vibrator 10 and is disposed at the rear surface of the piezoelectric vibrator 10. A material of the packing material 40 is not especially limited. However, for example, rubber having a good sound absorbency is used.

Flexible Printed Circuit

Figure 3:
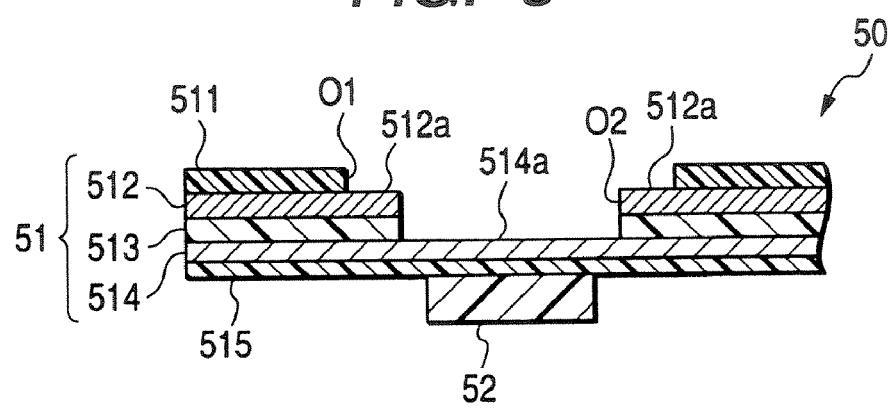
FIG. 3 is a schematic view of a flexible printed circuit according to the embodiment of the present invent.
Figure 4:
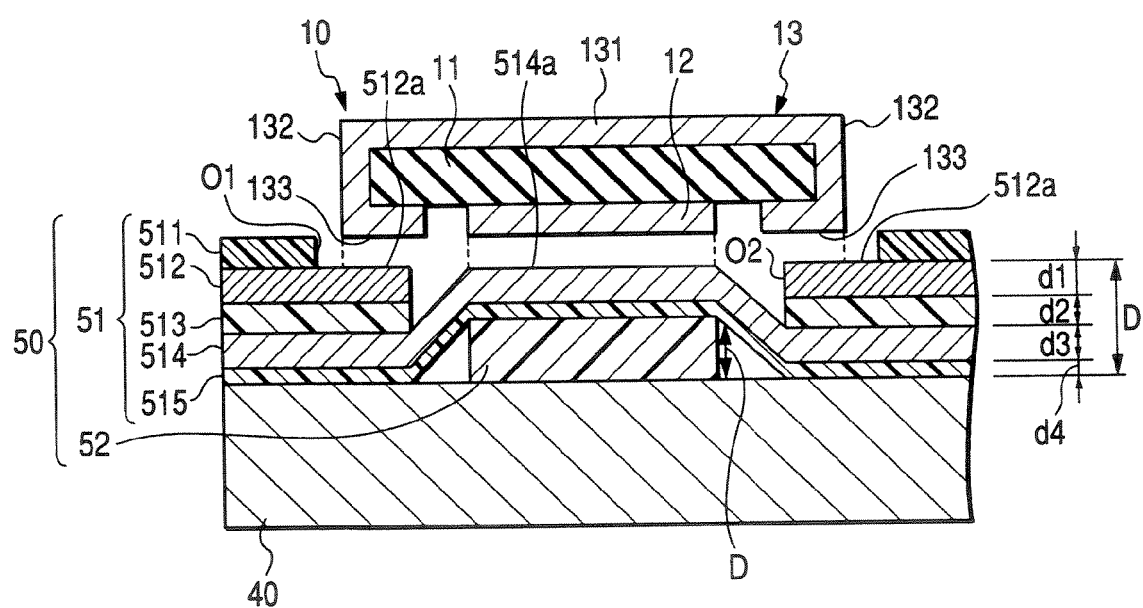
FIG. 4 is an exploded view of a piezoelectric vibrator, packing material, and a flexible printed circuit according to the embodiment of the present invent.

FIG. 3 is a schematic view of a flexible printed circuit 50 according to the embodiment of the invention, and FIG. 4 is an exploded view of the piezoelectric vibrator 10, the packing material 40, and the flexible printed circuit 50 according to the embodiment of the invention. In addition, the flexible printed circuit 50 in FIG. 3 is a state prior to a heat press process.

The flexible printed circuit 50 serves to transmit a driving signal toward the piezoelectric vibrator 10 or a reception signal from the piezoelectric vibrator 10, and the flexible printed circuit 50 is disposed between the piezoelectric vibrator 10 and the packing material 40.

As shown in FIG. 3 and FIG. 4, this flexible printed circuit 50 is configured of a main body 51 of the flexible printed circuit and a spacer 52. The main body 51 of the flexible printed circuit is configured of a first insulating layer 511, an earth wiring layer (a first wiring) 512, a second insulating layer 513, a signal wiring layer (a second wiring) 514, and a third insulating layer 515 that is sequentially laminated from the piezoelectric vibrator 10 toward the packing material 40.

The thickness of the earth wiring layer 512 is approximately equal to that of the signal wiring layer 514. In addition, thickness of the earth wiring layer 512 is referred to as d1, and the thickness of the signal wiring layer 514 is referred to as d3 in a following description. As a material of the earth wiring layer 512 and the signal wiring layer 514, metals such as copper having a good conductive property are used.

The first insulating layer 511 is configured such that the area slightly larger than a part corresponding to the rear surface of the piezoelectric vibrator 10 is removed in the lens direction. That is, an opening O1 slightly larger than the rear surface of the piezoelectric vibrator 10 is formed in the first insulating layer 511 in the lens direction.

The earth wiring layer 512 and the second insulating layer 513 are configured such that the area smaller than a part corresponding to the rear surface of the piezoelectric vibrator 10 and the area larger than a part corresponding to the signal electrode 12 is removed in the lens direction. That is, an opening O2 that is smaller than the rear surface of the piezoelectric vibrator 10 and is larger than the signal electrode 12 is formed in the earth wiring layer 512 and the second insulating layer 513 in the lens direction. For this reason, the signal wiring layer 514 is exposed from the flexible printed circuit 50 to the signal electrode 12 formed at the rear surface of the piezoelectric vibrator 10. In addition, the size of the opening O2 is smaller than that of the opening O1 formed in the first insulating layer 511. Accordingly, the earth wiring layer 512 is exposed to the two rear electrode portions 133 formed at the rear surface of the piezoelectric vibrator 10.

The spacer 52 is interposed between the packing material 40 and the flexible printed circuit 50 and serves to protrude a part corresponding to the signal electrode 12 of the piezoelectric vibrator 10 toward the piezoelectric vibrator 10. The forming range of the spacer 52 approximately corresponds to the forming range of the signal electrode 12 of the piezoelectric vibrator 10. However, anything will do as long as the forming range of the spacer 52 is limited to the inner side of the opening O2 formed in the earth wiring layer 512 and the second insulating layer 513, even though the forming range of the spacer 52 is larger or smaller than the signal electrode 12.

As shown in FIG. 4, the thickness D of the spacer 52 is set to the total thickness (d1+d2) of the thickness d1 of the earth wiring layer 512 and the thickness d2 of the second insulating layer 513 of the flexible printed circuit 50. Therefore, the thickness from the front surface of the packing material 40 to an exposed surface 514a of the signal wiring layer 514 becomes the total thickness (d1+d2+d3+d4) of the thickness d3 of the signal wiring layer 514, the thickness d4 of the third insulating layer 515, and the thickness (d1+d2) of the spacer 52. This is equal to the thickness from the packing material 40 to an exposed surface 512a of the earth wiring layer 512. That is, if the thickness D of the spacer 52 is set to the thickness (d1+d2), the exposed surface 512a of the earth wiring layer 512 and the exposed surface 514a of the signal wiring layer 514 may be included in the same plane.

In addition, the thickness D of the spacer 52 may be finely matched in accordance with the material of the spacer 52. That is, if the spacer 52 is formed of a soft material, the spacer 52 is slightly compressed by being interposed between the packing material 40 and the main body 51 of the flexible printed circuit. Accordingly, the thickness D of the spacer 52 may be set to the thickness (d1+d2+α) in advance by considering amount α of compression of the spacer 52.

Two rear electrode portions 133 of the earth electrode 13 are electrically connected to two exposed surfaces 512a of the earth wiring layer 512, respectively. In addition, the signal electrode 12 is electrically connected to the exposed surface 514a of the signal wiring layer 514.

Non-conductive bonding agent is used for the joint between the piezoelectric vibrator 10 and the flexible printed circuit 50. Materials of the non-conductive bonding agent are not especially limited, but resin such as an epoxy is used in the embodiment of the invention. The thickness of the non-conductive bonding agent is set to 5 μm or less.

Manufacturing Process of Flexible Printed Circuit

First, the first insulating layer 511, the earth wiring layer 512, the second insulating layer 513, the signal wiring layer 514, and the third insulating layer 515 are laminated. Then, this laminated body is pressurized by, for example, heat press. For this reason, the signal wiring layer 514 and the third insulating layer 515 are protruded toward the inner side of the opening O2 by a pressing force from the spacer 52. Therefore, the exposed surface 512a of the earth wiring layer 512 and the exposed surface 514a of the signal wiring layer 514 are set within the same plane. The flexible printed circuit 50 is completed by the above-described manufacturing process.

Process of Jointing Piezoelectric Vibrator 10 and Packing Material to Flexible Printed Circuit First, the bonding agent is applied on the front surface of the packing material 40. Then, the flexible printed circuit 50 is pressurized against to the packing material 40, and the packing material 40 and the flexible printed circuit 50 are jointed to each other.

Next, the non-conductive bonding agent is applied on the signal electrode 12 and the rear electrode portion 133 of the earth electrode 13 of the piezoelectric vibrator 10. At this time, the thickness of the non-conductive bonding agent is set to 5 μm or less. Then, the piezoelectric vibrator 10 is pressurized against to the flexible printed circuit 50, and the flexible printed circuit 50 and the piezoelectric vibrator 10 are jointed to each other. For this reason, the exposed surface 514a of the signal wiring layer 514 and the signal electrode 12 are electrically connected to each other, and the exposed surface 512a of the earth wiring layer 512 and the rear electrode portion 133 of the earth electrode 13 are electrically connected to each other. The process of jointing the piezoelectric vibrator 10 and the packing material 40 to the flexible printed circuit 50 is completed by the above-described jointing process.

Operations

In the flexible printed circuit 50 according to the embodiment of the invention, the exposed surface 514a of the signal wiring layer 514 and the exposed surface 512a of the earth wiring layer 512 are set within the same plane. For this reason, when the front surface of the flexible printed circuit 50 is closely bonded to the rear surface of the piezoelectric vibrator 10, no gap occurs between the signal electrode 12 and the signal wiring layer 514 or the rear electrode portion 133 of the earth electrode 13 and the earth wiring layer 512. Therefore, the non-conductive resin may be applicable for the adhesion between the piezoelectric vibrator 10 and the flexible printed circuit 50. As a result, since the soldering process used in the related art is not necessary, the piezoelectric body 11 of the piezoelectric vibrator 10 is not heated, and the deterioration of the piezoelectric body 11 is prevented in the manufacturing process.

The flexible printed circuit 50 according to the embodiment of the invention is interposed between the piezoelectric vibrator 10 and the packing material 40 to completely cover the entire rear surface of the piezoelectric vibrator 10. Accordingly, the notched portion for accommodating the end of the flexible printed circuit 50 is not formed in the packing material 40, as in the related art. As a result, when the piezoelectric vibrator 10 is pressurized against the packing material 40, the pressure applied to the piezoelectric vibrator 10 is not biased, and the piezoelectric vibrator 10 is not broken.

The piezoelectric vibrator 10 according to the embodiment of the invention includes two rear electrode portions 133 provided at the rear surface of the piezoelectric vibrator 10. That is, the earth electrode 13 according to the embodiment of the invention extends to both sides of the signal electrode 12 in the rear surface of the piezoelectric vibrator 10. Then, the earth wiring layer 512 of the flexible printed circuit 50 is exposed from the flexible printed circuit 50 at two positions corresponding to the rear electrode portions 133 of the earth electrode 13. For this reason, the earth electrode 13 of the piezoelectric vibrator 10 and the earth wiring layer 512 of the flexible printed circuit 50 are electrically connected to each other at two positions. Therefore, the joint reliability is largely improved as compared to the electric connection of the related art that is connected to each other at one position. In addition, as in the related art, since there is no need to form the metal plating electrode on the surface of the acoustic matching layer, the designed conditions of the acoustic matching do not fall into disorder, and the acoustic characteristics is not decreased. Such an effect is striking especially in a high frequency region.

Figure 5:
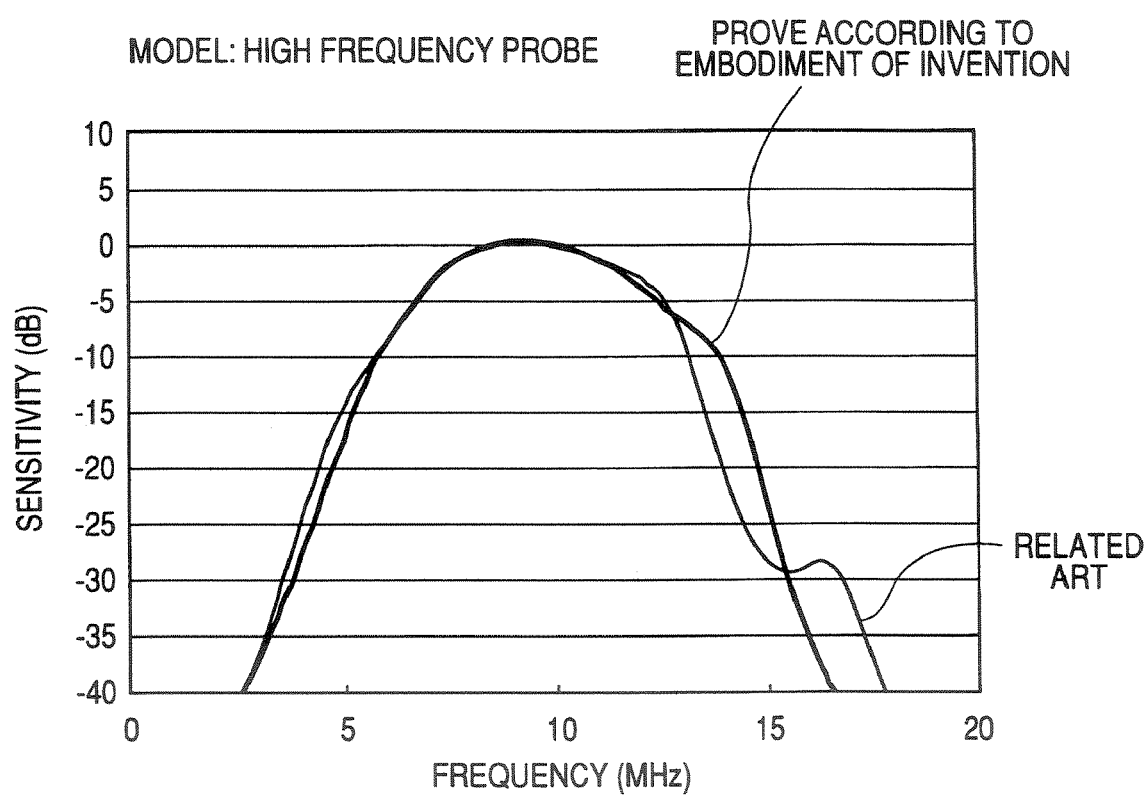
FIG. 5 is a view explaining effects according to the embodiment of the invention.

FIG. 5 shows the result of the simulation obtained by using the ultrasonic probe according to the embodiment of the invention and the related art ultrasonic probe. As shown in FIG. 5, according to the related art ultrasonic probe, the deterioration of the matching condition occurs due to the metal plating electrode formed on the surface of the acoustic matching layer in the region of high frequency (for example, the region of 12 MHz or more). Meanwhile, since the metal plating electrode is not formed on the surface of the acoustic matching layer in the ultrasonic probe according to the embodiment of the invention, it is possible to achieve good sensitivity in the region of high frequency.

In addition, according to the embodiment of the invention, the signal electrode 12 is formed at the rear surface of the piezoelectric vibrator 10, but the invention is not limited thereto. For example, if the piezoelectric vibrator is 2D array type, the signal voltage and the earth voltage applied to the front surface and the rear surface of the piezoelectric vibrator may be exchanged with each other. The invention is applicable to the ultrasonic probe having the piezoelectric vibrator of the above-mentioned 2D array type.

The invention is not limited to the specific details and representative embodiments shown and described herein. Accordingly, various modifications may be made without departing from the spirit or scope of the general inventive concept as defined by the appended claims and their equivalents. In addition, various inventions may be formed by properly combining a plurality of components disclosed in the embodiment of the invention. For example, some components may be removed from the entire components disclosed in the embodiment of the invention. Further, the components according to different embodiments may be properly combined.

What is claimed is:

1. An ultrasonic probe comprising:
a piezoelectric vibrator having a first electrode and a second electrode on a rear surface;
an acoustic matching layer disposed on a front surface of the piezoelectric vibrator;
a packing material disposed on the rear surface of the piezoelectric vibrator;
a flexible printed circuit that is interposed between the piezoelectric vibrator and the packing material to cover the entire rear surface of the piezoelectric vibrator and has a first wiring layer and a second wiring layer,
wherein the first wiring layer and the second wiring layer are exposed from a surface facing the piezoelectric vibrator of the flexible printed circuit so as to be electrically connected to the first electrode and the second electrode through an exposed surface of the first wiring layer and an exposed surface of the second wiring layer, respectively, and
wherein the exposed surface of the first wiring layer and the exposed surface of the second wiring layer are substantially located within the same plane; and
a spacer that is interposed between the flexible printed circuit and the packing material to cause a part of the flexible printed circuit to be protruded such that the exposed surface of the wiring layer disposed at a position remote from the piezoelectric vibrator out of the first wiring layer and the second wiring layer is positioned within the same plane as the exposed surface of the wiring layer disposed at a position in the vicinity of the piezoelectric vibrator out of the first wiring layer and the second wiring layer.

2. The ultrasonic probe according to claim 1, wherein the first electrode and the first wiring layer are bonded to each other by using non-conductive bonding agent having the thickness of 5 μm or less, and the second electrode and the second wiring layer are bonded to each other by using non-conductive bonding agent having the thickness of 5 μm or less.

3. An ultrasonic probe comprising:
a piezoelectric vibrator transmitting and receiving ultrasonic waves;
an acoustic matching layer disposed on a front surface of the piezoelectric vibrator;
a packing material disposed on a rear surface of the piezoelectric vibrator;
a flexible printed circuit that is interposed between the piezoelectric vibrator and the packing material to cover the entire rear surface of the piezoelectric vibrator and has a first wiring layer and a second wiring layer,
wherein the piezoelectric vibrator includes:
a piezoelectric body having a piezoelectric effect;
a first electrode formed at a part on a rear surface of the piezoelectric body; and
a second electrode having a first portion formed on a front surface of the piezoelectric body and a second portion formed on the rear surface of the piezoelectric body and positioned on both sides of the first electrode,
wherein the first wiring layer is exposed from the flexible printed circuit at a part facing the first electrode, and the second wiring layer is exposed from the flexible printed circuit at a part facing the second portion of the second electrode, and
wherein the first wiring layer and the second wiring layer are electrically connected to the first electrode and the second electrode through an exposed surface of the first wiring layer and an exposed surface of the second wiring layer, respectively, and wherein the exposed surface of the first wiring layer and the exposed surface of the second wiring layer are substantially located in the same plane; and a spacer that is interposed between the flexible printed circuit and the packing material to cause a part of the flexible printed circuit to be protruded such that the exposed surface of the wiring layer disposed at a position remote from the piezoelectric vibrator out of the first wiring layer and the second wiring layer is positioned within the same plane as the exposed surface of the wiring layer disposed at a position in the vicinity of the piezoelectric vibrator out of the first wiring layer and the second wiring layer.

4. The ultrasonic probe according to claim 3, wherein the first electrode and the first wiring layer are bonded to each other by using a non-conductive bonding agent having the thickness of 5 μm or less, and the second electrode and the second wiring layer are bonded to each other by using non-conductive bonding agent having the thickness of 5 μm or less.

5. An ultrasonic probe comprising:
a plurality of piezoelectric bodies;
a first electrode formed on a first surface of each piezoelectric body;
a second electrode having a first portion formed on the first surface of each piezoelectric body such that the first electrode is disposed therebetween, a second portion formed on a second surface opposite to the first surface of each piezoelectric body, and a third portion electrically connecting the first portion and the second portion to each other;
an acoustic matching layer disposed on a side of the second surface of each piezoelectric body;
a flexible printed circuit provided on a side of the first surface of each piezoelectric body and having a first wiring layer connected to each first electrode and a second wiring layer connected to each second electrode;
wherein the first wiring layer is wired so as to supply a driving signal to each first electrode and the second wiring layer is wired so as to earth the plurality of second electrodes;
wherein the first wiring layer has a first exposed surface facing the plurality of first electrodes, and the second wiring layer has a second exposed surface facing the plurality of second electrodes;
wherein the height of the first electrode in the first surface is substantially equal to that of the second electrode in the first surface; and
wherein the ultrasonic prove further includes a spacer for pushing up at least one of the first exposed surface and the second exposed surface such that the height of the first exposed surface and the second exposed surface is substantially equal to each other.

6. The ultrasonic probe according to claim 5, wherein the first electrode and the first wiring layer are bonded to each other by using non-conductive bonding agent having the thickness of 5 μm or less, and the second electrode and the second wiring layer are bonded to each other by using non-conductive bonding agent having the thickness of 5 μm or less.

7. An ultrasonic probe comprising:
a piezoelectric vibrator including a piezoelectric body, a first electrode located at least in an end portion of a rear surface of the piezoelectric body, and a second electrode located in a central portion of the rear surface of the piezoelectric body;
an acoustic matching layer disposed on a front surface of the piezoelectric vibrator;
a backing material disposed on a rear surface of the piezoelectric vibrator; and
a flexible printed circuit that is interposed between the piezoelectric vibrator and the backing material to cover the entire rear surface of the piezoelectric vibrator and has a first wiring layer and a second wiring layer, at least a part of which is located in a position lower than the first wiring layer,
wherein the first wiring layer and the second wiring layer are exposed through a portion of a surface of the flexible printed circuit that faces the piezoelectric vibrator,
the ultrasonic probe further comprising a spacer which protrudes at least a part of the second wiring layer to make the first wiring layer and the second wiring layer substantially the same in height in the exposed portion,
the first wiring layer and the first electrode being electrically connected in the exposed portion and
the second wiring layer and the second electrode being electrically connected in the exposed portion.

* * * * *